US00PP28950P2

(12) United States Plant Patent
Egger

(10) Patent No.: US PP28,950 P2
(45) Date of Patent: Feb. 6, 2018

(54) ***AGASTACHE* PLANT NAMED 'TNAGAPDB'**

(50) Latin Name: ***Agastache* hybrid**
Varietal Denomination: TNAGAPDB

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/330,802

(22) Filed: Nov. 7, 2016

(51) Int. Cl.
*A01H 5/02* (2006.01)

(52) U.S. Cl.
USPC ..... Plt./399

(58) Field of Classification Search
USPC ..... Plt./263.1, 399
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct form of *Agastache* plant characterized by purple blue flowers in large inflorescences, a long bloom time, a very short, compact habit, and excellent vigor.

1 Drawing Sheet

Botanical denomination: *Agastache* hybrid.
Variety designation: 'TNAGAPDB'.

BACKGROUND OF THE INVENTION

The present invention relates to a new and distinct cultivar of *Agastache*, given the name, 'TNAGAPDB'. *Agastache* is in the family Lamiaceae. This new cultivar is one of several selections of new *Agastache* using hardy and dwarf *Agastache* species in the breeding lines to provide hardiness and compactness. The new cultivar is a selection from the open pollinated seedlings of *Agastache* 66-04. The new cultivar was selected for its compact habit, hardiness, and dark blue flowers.

Compared to the seed parent, *Agastache* 66-04 the new cultivar is shorter.

Compared *Agastache* 'Violet Vision' (U.S. Plant Pat. No. 25,274), the new cultivar has darker blue flowers and is shorter and more compact.

Compared *Agastache* 'Kudos Silver Blue' (U.S. Plant Pat. No. 25,344), the new cultivar has purple blue flowers rather than silver blue and is shorter and more compact.

This plant exhibits the following characteristics that make it unique:

1. purple blue flowers in large inflorescences,
2. a long bloom time,
3. a very short, compact habit, and
4. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows the new cultivar (with a white background) grown in a one gallon container in full sun in Canby, Oreg.

FIG. 2 shows a nine-month-old *Agastache* 'TNAGAPDB' growing in the trial field in mid-summer in Canby, Oreg.

DETAILED PLANT DESCRIPTION

The following is a detailed description of the new *Agastache* cultivar based on observations of 9-month-old specimens in early November growing in full sun in one gallon containers in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on The Royal Horticultural Society Colour Chart, 5$^{th}$ edition, 2007.

Plant:

*Form*.—Upright.
*Type*.—Herbaceous perennial.
*Cold hardiness*.—USDA Zone 6-10.
*Size*.—Grows to 32 cm wide and 30 cm tall to the top of the flowers.
*Vigor*.—Excellent.
*Branching*.—About 11 main stems from the base, these branch at every node.
*Stem*.—Square in cross section, grows to 6 mm wide and 20 cm tall to the first flower, pubescent, internodes range from 1 to 3 cm long, Yellow Green 146A.
*Roots*.—White 155B, fibrous, plants root easily from stem tip cuttings.

Leaf:

*Type*.—Simple.
*Arrangement*.—Opposite.

*Shape*.—Ovate, sometimes cupping upwards.
*Venation*.—Pinnate.
*Margins*.—Coarsely serrate.
*Apex*.—Acute to obtuse.
*Base*.—Cuneate to auriculate.
*Blade size*.—Grows to 45 mm long and 38 mm wide.
*Surface texture*.—Pubescent on both sides.
*Petiole description*.—Grows to 18 mm long and 2 mm wide, pubescent, Yellow Green 147B.
*Leaf color*.—Top side Green N137A with vein Green 137C, bottom side closest to Yellow Green 147B with vein 147C.
*Fragrance*.—Aromatic.

Inflorescence:
*Type*.—Terminal spike with up to 11 congested whorls.
*Number of flowers*.—Up to 600 per spike.
*Size of inflorescence*.—Grows to 13 cm tall and 3.3 cm wide.
*Peduncle*.—Grows to 3 cm tall and 2.5 mm wide, pubescent, Yellow Green 146A.
*Pedicel*.—Grows to 2 mm long, pubescent, Yellow Green 138B.
*Bloom period*.—June through frost in Canby, Oreg.

Flower bud:
*Size*.—9 mm long and 3 mm wide at the widest point prior to opening.
*Description*.—Tubular.
*Surface texture*.—Pubescent.
*Color*.—Violet Blue 92A.

Flower:
*Type*.—Zygomorphic.
*Shape*.—Bilabiate, tubular.
*Size*.—20 mm long and 8 mm wide.
*Corolla description*.—18 mm long and spreads to 8 mm wide; color both sides Violet N87A; pubescent inside and outside, tube 14 mm long and 1 mm to 4 mm wide; 2 upper lobes joined, each 3 mm long and 3 mm wide, each ovate, tips obtuse, margin entire; three lower lobes, two spreading sideways and curl back, each 4 mm long and 3 mm wide, tip obtuse, margin entire; bottom lobe, reflexed, broadly obovate, notched at the tip, margin irregularly crenulate, 6 mm wide and 3.5 mm deep.
*Calyx description*.—Campanulate, 6 mm long and 3 mm wide, pubescent outside and glabrous inside, 5 lobed, lobes ovate, 2 mm long, entire, acute, colored when young Greyed Orange 177A at tip blending to Yellow Green 147C becoming Yellow Green 147C all over with age.
*Pistil description*.—22 mm long, ovary 1 mm long, Yellow Green 145D, style 21 mm long, bottom half White NN155B darkening on top half to Violet N87A, stigma two-parted, 1 mm deep, Violet N87C.
*Stamen description*.—4 in number, paired and exerted, top two 7 mm long and bottom two 5 mm long, filaments Violet 86A, anthers 0.5 mm long, Greyed Orange 187A, pollen White N155A.
*Fragrance*.—Aromatic.
*Lastingness*.—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

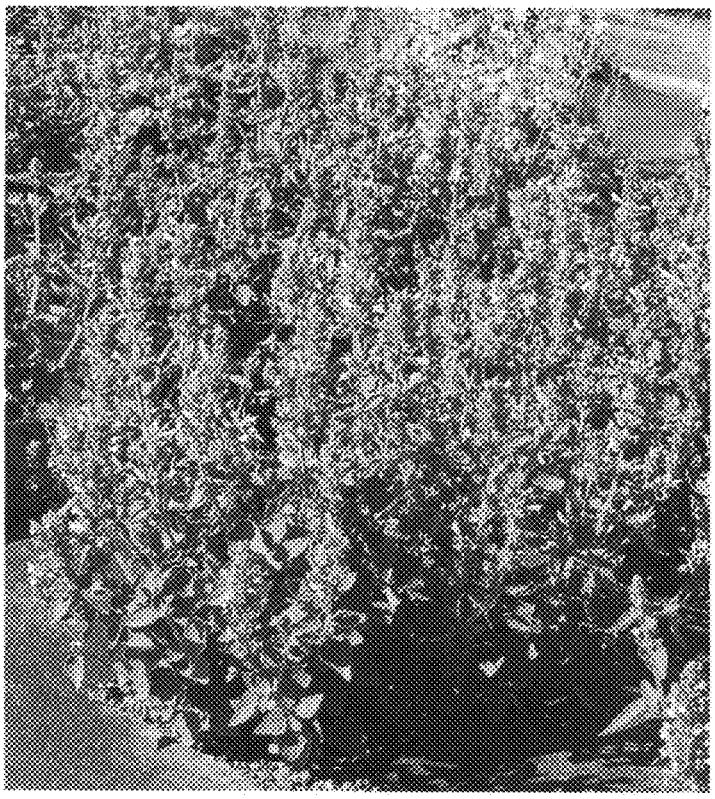

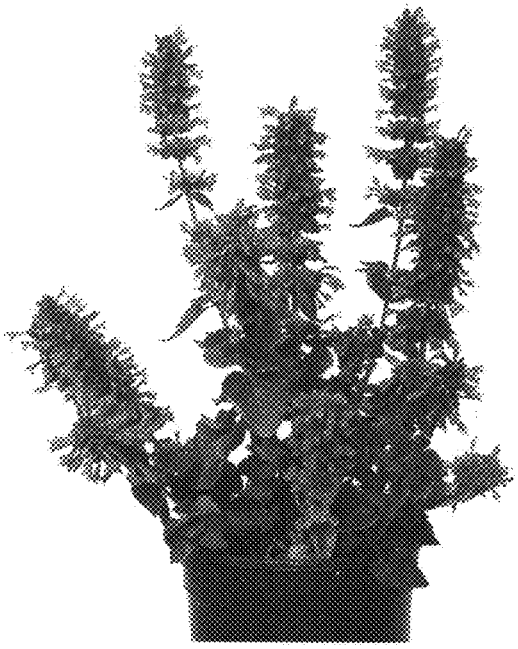
FIG. 1 on left
FIG. 2 below